(12) United States Patent
Goertz et al.

(10) Patent No.: US 7,063,822 B2
(45) Date of Patent: Jun. 20, 2006

(54) DENTAL HYGIENE UNIT

(76) Inventors: Linda S. Goertz, 20955 Tejas Trail West, San Antonio, TX (US) 78257; George A. Schultz, 176 Ohio, New Braunfels, TX (US) 78130

( * ) Notice: Subject to any disclaimer, the term of this patent is extended or adjusted under 35 U.S.C. 154(b) by 290 days.

(21) Appl. No.: 10/661,188

(22) Filed: Sep. 12, 2003

(65) Prior Publication Data
US 2005/0058583 A1 Mar. 17, 2005

(51) Int. Cl.
*A61L 2/18* (2006.01)

(52) U.S. Cl. .................. 422/300; 206/209.1; 312/206; 211/66

(58) Field of Classification Search ............. 206/209.1, 206/210; 422/300
See application file for complete search history.

(56) References Cited

U.S. PATENT DOCUMENTS

| | | | | |
|---|---|---|---|---|
| 1,507,466 A | * | 9/1924 | Collins | .............. 206/209.1 |
| 1,556,148 A | * | 10/1925 | Knott | .............. 206/209.1 |
| 3,019,494 A | * | 2/1962 | Horie et al. | .............. 206/208 |
| 3,881,868 A | * | 5/1975 | Duke | .............. 206/209.1 |
| 4,927,011 A | * | 5/1990 | Wilkinson | .............. 206/217 |
| 5,522,497 A | * | 6/1996 | Stacy | .............. 206/209.1 |

* cited by examiner

*Primary Examiner*—E. Leigh McKane
(74) *Attorney, Agent, or Firm*—Michelle Evans; Gunn & Lee, P.C.

(57) ABSTRACT

A storage device for sterilizing and storing dental appliances, oral hygiene devices or dental brushes is shown. A vase type container has an opening for receiving dental appliances or oral hygiene devices therein. A sterilization bath container is suspended in the opening. Holes around the opening allow oral hygiene devices or dental brushes to be suspended therearound. Dental appliances, oral hygiene devices or dental brushes are dipped in the sterilization bath and placed inside the vase-type container. Oral hygiene devices or dental brushes are dipped in the sterilization bath prior to being suspended in the holes or placed in the vase-type container. A top is placed over the opening for sealing the sterilization bath and covering dental appliances, oral hygiene devices or dental brushes while allowing fresh air access thereto.

12 Claims, 5 Drawing Sheets

DENTAL HYGIENE UNIT

BACKGROUND OF THE INVENTION

1. Field of the Invention

The present invention relates to a dental hygiene unit and, more particularly, to a unit that provides for sterilization of dental appliances, oral hygiene devices or dental brushes; sealing of a sterilization bath; covering of the dental appliances, oral hygiene devices or dental brushes as stored and fresh air access thereto.

2. Background Information

In recent years, there has been more emphasis on oral hygiene by the general population. As part of the increased emphasis on oral hygiene, most of the general population makes regular visits to their dentist for cleaning of their teeth and a general dental examination. Simultaneously, emphasis has been given by dentists, dental organizations and health organizations of the importance of maintaining healthy teeth.

Many different types of dental prostheses are used in the maintenance of healthy teeth. Even for someone who has all of their teeth, invisible retainers are quite common, which invisible retainers may periodically be removed. Also, partial removable dentures are commonly located in the mouth of a person who has missing teeth. The partial removable dentures may typically be removed in the evening or on other occasions. Retainers are quite common for straightening teeth or holding teeth in a particular configuration. Retainers may periodically be removed by the user.

For athletes, mouth guards are commonly used, especially athletes who have braces. While in the process of straightening teeth, headgear may even be used along with braces. Splints, dentures and mouth guards are also used.

For younger persons, teething rings and pacifiers are commonly inserted in the mouth. For older people, snore guard appliances are also inserted in the mouth.

Many different types of brushes are used in maintaining healthy teeth in addition to the use of a standard toothbrush. Brushes, including gun brushers and stimulators may have various types of heads to get into space in and around the teeth. Even a handheld flosser may be used in helping to clean the mouth. Tongue scrapers are even utilized to help maintain proper hygiene in the mouth. All of these dental appliances, oral hygiene devices or dental brushes should be sterilized and maintained in a sterile condition. No device known by applicant provides for the sterilization and storage of these different types of dental appliances, oral hygiene devices or dental brushes.

There has been considerable emphasis in the past on brushing teeth. To prompt someone to brush their teeth, normally the toothbrush is stored at a convenient location that is readily accessible in the bathroom. In the past, toothbrushes have either been stored hanging from the bristles in an open air environment or in an enclosed sanitary bath or atmosphere. Neither of those is entirely satisfactory. In the open exposed environment, anything has access to the toothbrush. While it is good for the toothbrush to dry between uses, open air access thereto is not the ideal way of storing a toothbrush because it allows flies, roaches, ants or other insects access to the toothbrush.

On the other hand, storing a dental brush while dipped in some type of disinfectant or in an enclosed disinfectant atmosphere continually allows moisture to the dental brush. In that manner, the dental brush never has a chance to dry between uses to maintain a good firm bristles. Moisture can even cause bacteria or other microorganisms to grow in the toothbrush. The idea solution would be to have some type of holder that would allow fresh air ventilation to the bristles of the dental brush, but at the same time allowing for the dental brush to be sanitized in some type of sanitation bath.

Just as with dental brushes, dental appliances and oral hygiene devices have many of the same needs as a dental brush, namely, to be sanitized and stored. For a dental appliance, such as partial removable dentures, retainers, dentures, or dental prosthesis that may be removed, there is a need to periodically sanitize and store the dental appliance. Just as a dental brush needs some type of sanitation bath, so does the dental appliance. Also, the dental appliance needs to be stored in a sanitary manner, rather than being left on an open shelf in the bathroom.

Applicant is aware of a number of different types of toothbrush holders, none of which can be used for dental appliances or oral hygiene devices like the present invention. U.S. Pat. No. 1,507,466 shows a toothbrush holder that has a disinfectant located in the bottom thereof. There is no suggestion of dipping the toothbrush in the disinfectant. Fumes from the disinfectant allegedly sterilize the toothbrush.

U.S. Pat. No. 2,038,941 shows a wall mounted toothbrush holder with a cover over the head of the toothbrush. An antiseptic or disinfectant is located within the holder so the fumes allegedly disinfect the head of the toothbrush.

U.S. Pat. No. 2,280,431 also shows a toothbrush holder with a disinfectant that creates fumes inside of the holder that allegedly sterilizes the toothbrush.

U.S. Pat. No. 3,881,868 shows a combination toothbrush sterilizer and holder. Again, fumes from an antiseptic fill the container in which the toothbrush is stored and supposedly sterilizes the toothbrush.

One of the more common methods of storing toothbrushes today is having some type of container with a sterilization bath in the bottom thereof and, by picking up a portion of the container, the toothbrushes will be raised out of the sterilization bath. Such an arrangement is shown in U.S. Pat. No. 3,904,362 to DiPaolo, and U.S. Pat. No. 1,566,860 to Hainzigianis. A similar type patent is shown in U.S. Pat. No. 5,566,823 to Summers.

Other patents that may be of interest are U.S. Pat. No. 4,997,629 to Marchand; Des. 323,090 to Santarelli; and U.S. Pat. No. 4,915,219 to Ottimo. Further, U.S. Patent Application Publication US 2002/0031461 A1 to Knipp, published on Mar. 14, 2002, shows another type of toothbrush holder. None of the patents that applicant is aware of shows a combination of toothbrush and dental appliance sanitation and storage device.

SUMMARY OF THE INVENTION

It is an object of the present invention to provide a unit for sanitizing and storing dental appliances, oral hygiene devices or dental brushes.

It is another object of the present invention to provide a unit that has a means for sterilizing dental appliances, oral hygiene devices or dental brushes, sealing of the sterilization bath, covering of the items as stored, and allowing fresh air access to the items while stored.

It is still another object of the present invention to provide a decorative hand-blown glass container in which dental appliances, oral hygiene devices or dental brushes may be stored in the bathroom.

It is yet another object of the present invention to provide a dental appliance, oral hygiene device or dental brush unit wherein the item may be sterilized and then placed inside of the container, which container has a lid that simultaneously seals the sterilization bath, covers the item, yet allows fresh air access to the toothbrush.

These and other objects of the present invention are accomplished by a dental appliance, oral hygiene device and dental brush storage unit as described hereinbelow. The principal items that can be seen by a visitor in the bathroom would be a decorative vase-type container with a lid. The vase-type container and lid may be made from hand-blown colored glass. The upper part of the vase-type container has an opening through which a raised shelf may be placed in the bottom of the vase-type container.

Suspended across the opening by a horizontal flange is a sterilization bath container in which a sterilization fluid may be placed. A dental appliance or oral hygiene device may be dipped into the sterilization bath and then placed inside of the vase-type container either against the wall or on the raised shelf. The sterilization bath container has a generally flat upper opening. Holes are contained in the horizontal flange through which handles of toothbrushes may be suspended down into the vase-type container or air can flow to the inside of the vase-type container. Typically, an oral hygiene device or dental brush would be dipped into the sterilization bath and then suspended through the holes in the horizontal flange of the sterilization bath container.

Over the sterilization bath container and the upper opening of the vase-type container is located the lid that simultaneously seals the sterilization bath in the sterilization bath container and covers the oral hygiene devices or dental brushes suspended in the holes contained in the horizontal flange yet allows fresh air access to the oral hygiene devices or dental brushes for drying. The fresh air access is allowed in such a manner so that flies and other insects will not normally get on the oral hygiene devices or dental brushes.

One design provides for a lip inside the upper opening of the vase-type container on which the horizontal flange rests. In another alternative design, the horizontal flange simply rests on the upper surface of the vase-type container.

In actual use, the user will lift the lid off of the dental hygiene unit and reach for either the oral hygiene device or dental brush. If the dental appliance is the item wanted, the entire sterilization bath container has to also be removed to reach inside the vase-type container for the dental appliance. Depending on the size, the oral hygiene device may also be in the vase-type container. If only the dental brush is desired, simply removal of the lid will normally allow access to the dental brush. For example, the user can then brush their teeth and, after they are through, dip the bristles of the dental brush into the sterilization bath. Thereafter, the dental brush is suspended in the holes of the horizontal flange and the lid placed back in the top of the dental hygiene unit. The lid will simultaneously seal the sterilization bath, covering the dental brush while allowing fresh air access thereto.

While it is envisioned that the lid and the vase-type container may be made from decorative material, such as colored hand-blown glass, the raised shelf or the sterilization bath container may be of less expensive material, such as injection molded plastic. The lid and the vase-type container can also be made of injection molded plastic, but it is preferred that a more decorative type of material, such as hand-blown glass, be utilized. Naturally, the lid would include as part of the hand-blown glass, a handle or grip on the upper part thereof. Also, the lid will have on the underside thereof a flexible sealing material to seal the upper opening of the sterilization bath container.

DESCRIPTION OF THE PREFERRED EMBODIMENT

Figure 1:
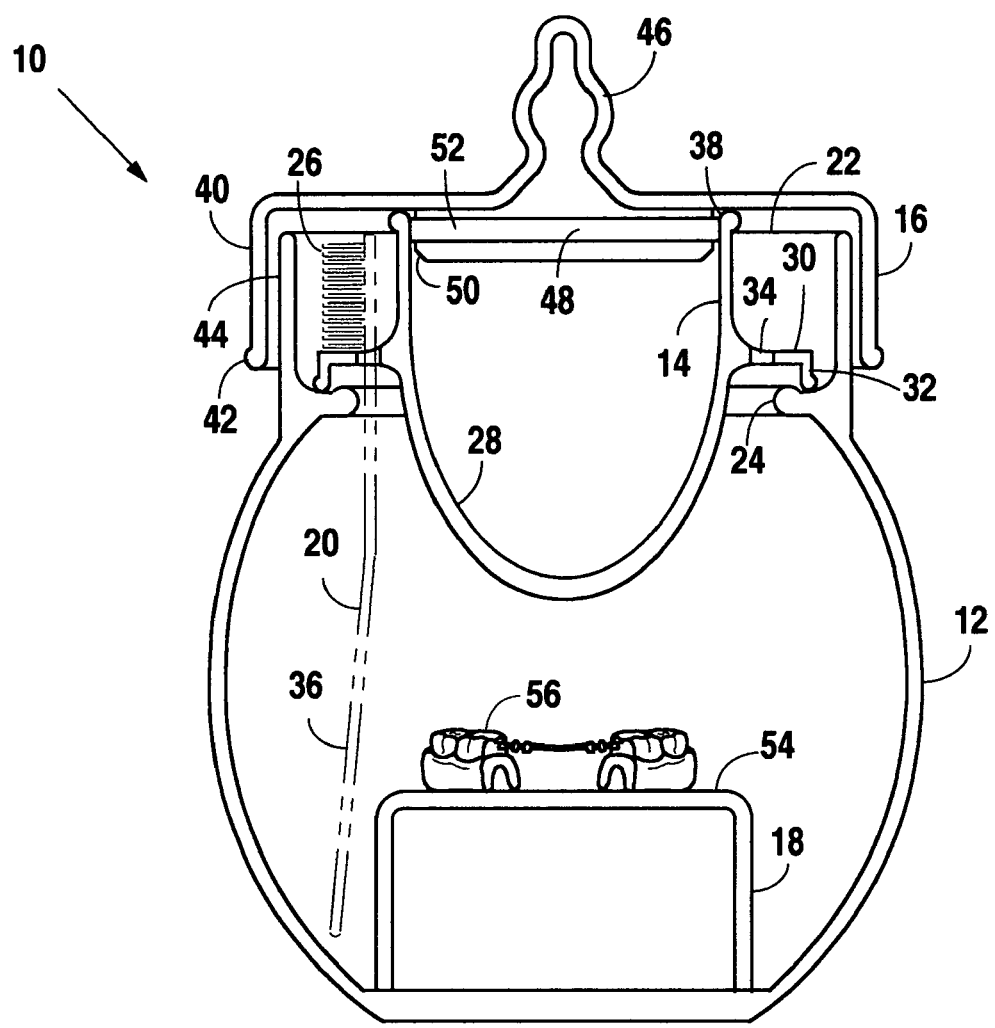
FIG. 1 is an elevated cross-sectional view of the present invention with a dental brush and a partial denture illustrated therein.
Figure 2:
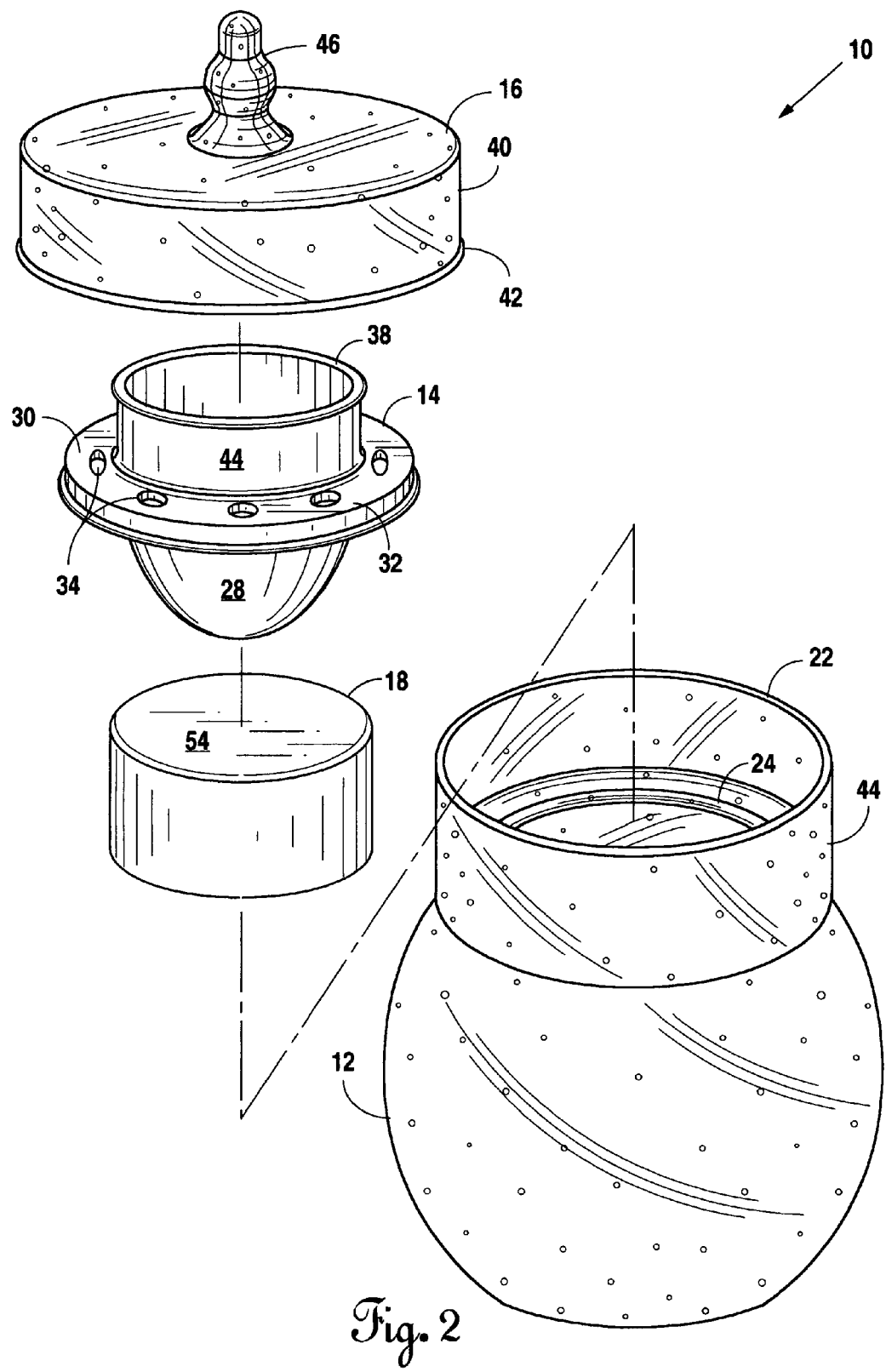
FIG. 2 is an exploded perspective view of the dental hygiene unit as shown in FIG. 1.

Referring to FIGS. 1 and 2 in combination, the dental hygiene unit is represented generally by reference numeral 10. The dental hygiene unit 10 is made up of a vase-type container 12, sterilization bath container 14, lid 16, and dental appliance/oral hygiene storage unit 18. Vase-type container 12 should be deep enough to accommodate toothbrushes 20 therein. Vase-type container 12 has an upper opening 22 and an inward lip 24 located therebelow. The distance between upper opening 22 and inward lip 24 is of sufficient space to accommodate the bristles portion 26 of the toothbrushes 20 therein between as is illustrated in FIG. 1.

Located within upper opening 22 of the vase-type container 12 is the sterilization bath container 14. Sterilization bath container 14 has a bowl 28 in which a sterilization bath may be retained. Extending outward from bowl 28 is a horizontal extension 30 that overlaps the inward lip 24. Horizontal extension 30 has a downward flare 32 for supporting the sterilization bath container 14 from the inward lip 24 of the vase-type container 12.

Periodically spaced around the horizontal extension 30 are holes 34 through which the handle portion 36 of the toothbrushes 20 or other oral hygiene devices may be inserted. Holes 34 are large enough for handle portion 36 of toothbrushes 20 or other oral hygiene devices (not shown) to be inserted therein, but is not large enough for bristles portion 26 or other enlarged portion of an oral hygiene device to go therethrough. Bowl 28 has an upper rim 38 therearound.

Referring now to lid 16, it has a downward flange 40 having on the lower end thereof an outward flare 42. Downward flange 40 is slightly larger than an upper cylinder portion 44 of the vase-type container 12 to allow air circulation therebetween. Upper cylinder portion 44 of the vase-type container 12 encircles bristles portion 26 of the toothbrushes 20 or any other dental brush, but simultaneously allows air circulation to bristles portion 26.

In the upper center of lid 16 is a knob 46 that can be used to remove the lid 16. While knob 46 is shown a particular shape, any particular shaped knob or handle may be utilized. On the underside of lid 16 and below knob 46 is flexible sealing material 48 that seals the upper rim 38 of bowl 28 of sterilization bath container 14. In the preferred embodiment, sealing material 48 should be flexible enough to provide a good seal of the sterilization bath container 14 and at the same time meet all governmental approvals for this type of usage. Sealing material 48 may have a lower beveled portion 50 to center lid 16 over the sterilization bath container 14, as well as a flexible portion 52 for sealing to the inside of the upper rim 38. Sealing material 48 may be attached to lid 16 by a glue that meets Food & Drug Administration regulations.

Contained inside of the vase-type container 12 is a dental appliance/oral hygiene device storage unit 18, which may be of any particular configuration, as long as it may be inserted and removed through upper opening 22 as defined by inward lip 24 of the vase-type container 12. In the preferred embodiment, dental appliance/oral hygiene device storage unit 18 is simply a circular type stool having a flat upper surface 54 on which a dental appliance, such as partial denture 56, may be placed. In the preferred embodiment, partial denture 56 is dipped in a sterilization bath contained in sterilization bath container 14 prior to being placed on flat upper surface 54 of dental appliance storage unit 18 inside of the vase-type container 12.

In actual use, when a person goes into the bathroom to perform an oral hygiene function, such as to brush their teeth, they will remove lid 16 and use toothbrush 20 to brush their teeth. After they are through and bristles portion 26 has been rinsed under the water faucet, then bristles portion 26 will be dipped into a sterilization bath contained in sterilization bath container 14 and the toothbrush 20 suspended through hole 34 and lid 16 replaced as is illustrated in FIG. 1. If the person has a dental appliance, such as partial denture 56, and wants to remove the partial denture 56 in the evening, lid 16 would be removed and sterilization bath container 14 picked up so the individual could reach inside of the vase-type container 12 to replace or remove partial denture 56. Prior to storing partial denture 56 on the dental appliance storage unit 18 inside of the vase-type container 12, the individual will normally dip partial denture 56 in the sterilization bath contained in sterilization bath container 14 prior to storage. Thereafter, the sterilization bath container 14 is again placed in upper opening 22 of the vase-type container 12 and lid 16 returned to its normal location.

Figure 3:
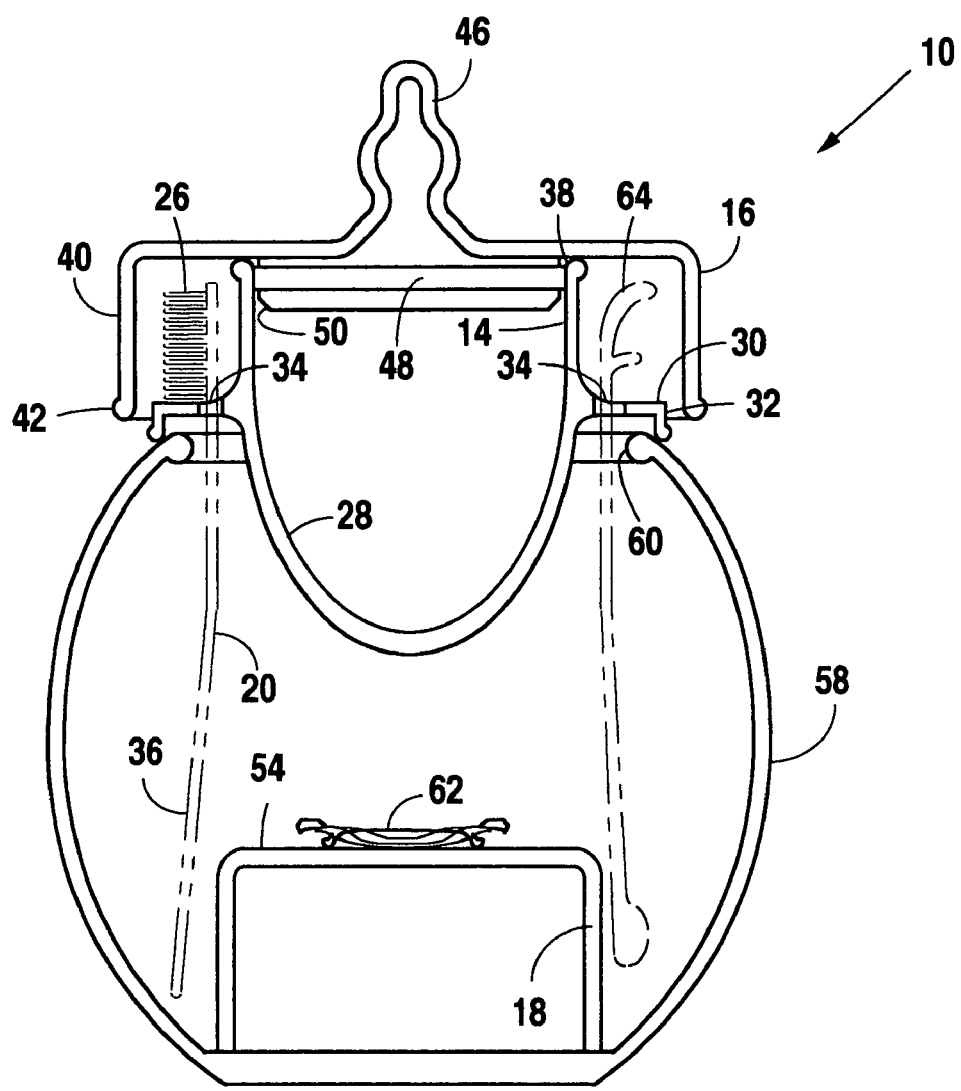
FIG. 3 is an elevated cross-sectional view of an alternative dental hygiene unit, with a dental brush, handheld flosser and a retainer illustrated therein.
Figure 4:
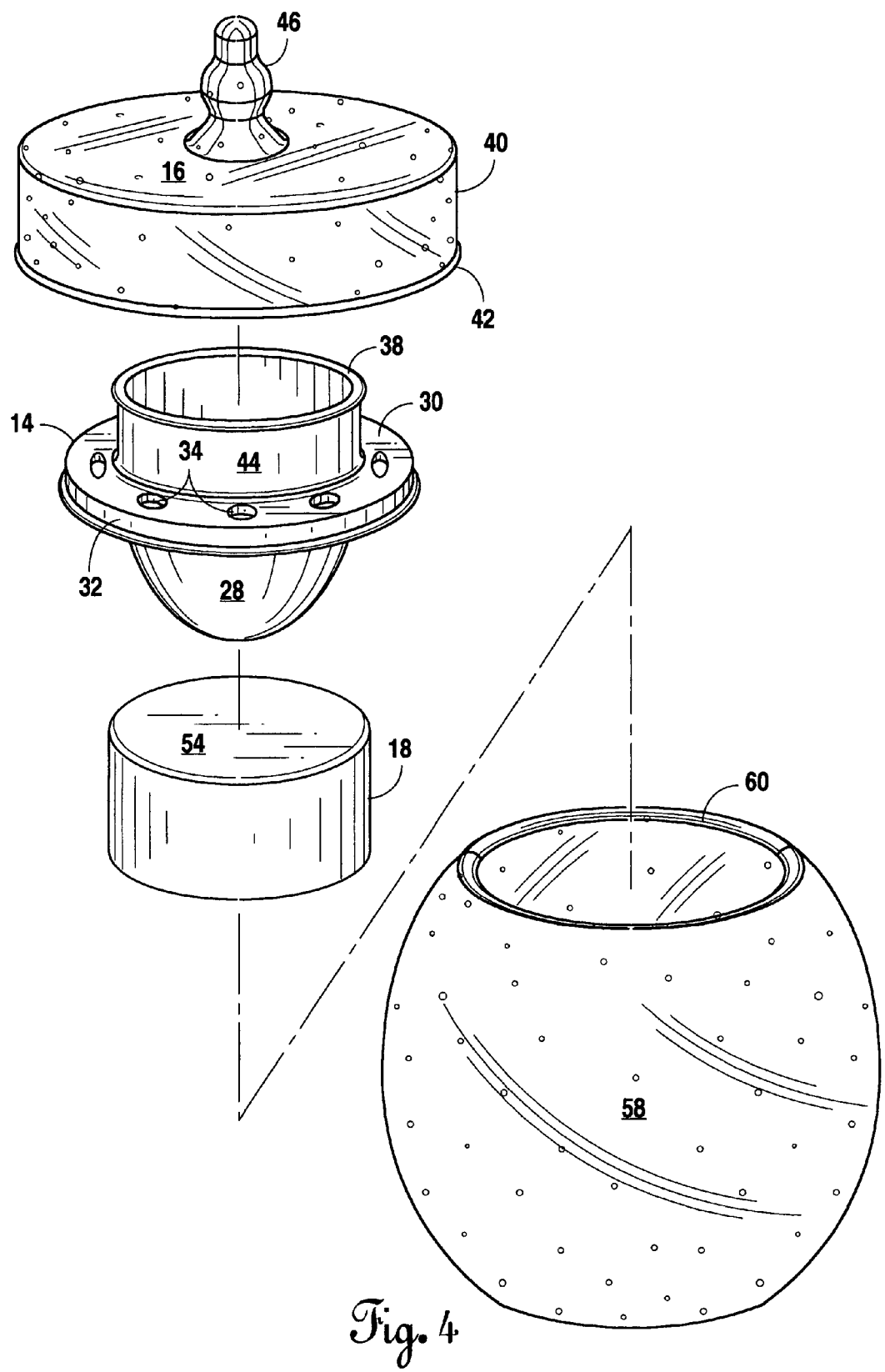
FIG. 4 is an exploded perspective view of FIG. 3.

Referring now to FIGS. 3 and 4 in combination, an alternative design of the dental hygiene unit is shown. Like numerals where appropriate will be used for the alternative design. Since the sterilization bath container 14, lid 16 and dental appliance/oral hygiene device storage unit 18 are identical in both embodiments, like numerals will be utilized to indicate like components. The vase-type container 58 shown in FIGS. 3 and 4 is different from the vase-type container 12 as shown in FIGS. 1 and 2. The vase-type container 58 has an upper opening 60. In this particular design, the vase-type container 58 does not include an upper cylinder portion 44 nor an inward lip 24 as shown in prior FIGS. 1 and 2. In this particular vase-type container 58, downward flare 32 of the horizontal extension 30 of sterilization bath container 14 simply rests on the top of the upper vase-type container 58 around the upper opening 60. The horizontal extension 30 with downward flare 32 is slightly larger than the upper opening 60. This particular alternative design allows more fresh air to flow to bristles portion 26 of toothbrushes 20, while at the same time providing a cover to protect the bristles portion 26 from flies and other insects. Also, a handheld flosser 64 is suspended through hole 34.

On dental appliance/oral hygiene storage unit 18 is located a retainer 62, which may periodically be removed and stored inside of hygiene unit 10 after proper sanitation in a sterilization bath of sterilization bath container 14.

In both of the designs as shown in FIGS. 1 and 2 or FIGS. 3 and 4, it is envisioned that dental hygiene unit 10 would be very decorative to the eye and pleasing to user. Dental hygiene unit 10 may be located on the counter in the bathroom as a decorative item. Lid 16 and the vase-type container 12 or 58 may be of hand-blown glass having many different decorative colors therein. The hand-blown glass makes an attractive display on the bathroom counter, while at the same time concealing and storing toothbrushes 20 and dental appliances, such as partial denture 56, retainer 62 or handheld flosser 64 therein. The sterilization bath as contained in sterilization bath container 14 is easy to reach for sterilization of either the dental appliances, oral hygiene devices or dental brushes. At the same time, the entire dental hygiene unit 10 may be disassembled for ease of cleaning.

Figure 5A:
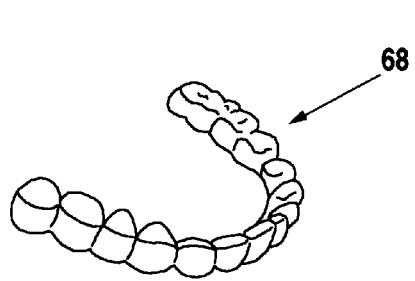
FIG. 5A–FIG. 5E are perspective views of typical dental appliances, including an invisible retainer, partial removable dentures (side and front), retainer, and mouth guard.
Figure 5B:
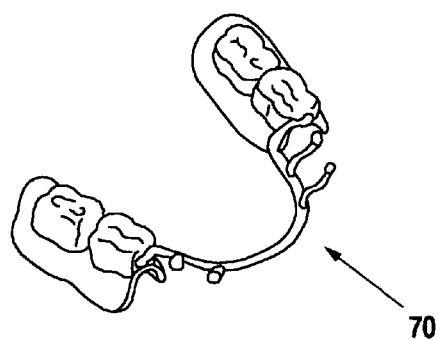

FIGS. 5a–5e gives examples of various types of dental appliances or oral hygiene devices that may be stored inside of the dental hygiene unit 10. FIG. 5a shows an invisible retainer 68 that may periodically be placed over a user's teeth. The invisible retainer 68 is a preferred dental appliance because it does not have the unsightly view of retainers, wires or braces. FIG. 5b shows a removable partial denture 70 that may be put in or taken out depending upon the preference of the particular user. The removable partial denture 70 is for the four rearmost teeth on either the top or bottom of the user.

Figure 5C:
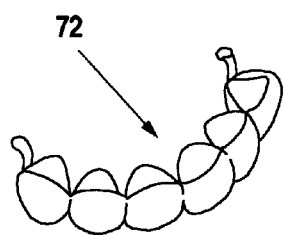

FIG. 5c illustrates a removable partial denture 72 where the front teeth of the user may be inserted or removed.

Figure 5D:
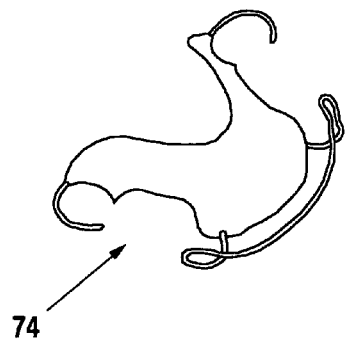

FIG. 5d shows a retainer 74 that may be worn for straightening or retaining of teeth in position.

Figure 5E:
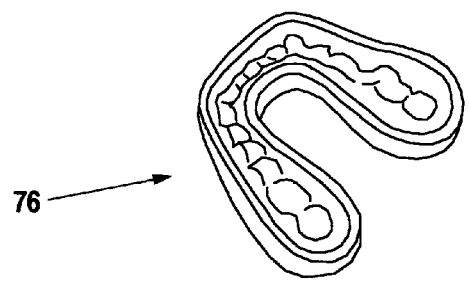

FIG. 5e is a mouth guard of the type commonly worn by athletes while participating in sports. All of the dental appliances or oral hygiene devices as shown in FIGS. 5a–5e may be sterilized in the sterilization bath of the sterilization bath container 14 prior to storage inside of dental hygiene unit 10. Obviously, many other different types of dental appliances, oral hygiene devices or dental brushes may be sterilized and stored inside dental hygiene unit 10.

We claim:

1. A dental hygiene holding apparatus in which dental appliances, oral hygiene devices or dental brushes may be sterilized in a sterilization bath and stored in said apparatus comprising:

a container having a flat lower surface and an upper opening large enough to receive dental appliances or oral hygiene devices therethrough;

a sterilizing bath container for holding a sterilization bath therein removably suspended in said upper opening;

a generally horizontal extension between said upper opening of said container and said sterilization bath container, said generally horizontal extension having holes therein for suspension of the dental appliances, oral hygiene devices or dental brushes after sterilization in said sterilization bath and wherein said generally horizontal extension extends outwardly from said sterilization bath container over said upper opening when said sterilization bath container is suspended in said upper opening; and a lid for simultaneously (a) sealing said sterilization bath in said sterilization bath container, (b) covering the dental appliances, oral hygiene devices or dental brushes as suspended in said holes, and (c) allowing fresh air to the dental appliances, oral hygiene devices or dental brushes, wherein an upper rim of said sterilization bath container holds said lid spaced above said container thereby allowing fresh air to contact the dental appliances, oral hygiene devices or dental brushes.

2. The dental hygiene holding apparatus as recited in claim 1 further includes a dental appliance/oral hygiene storage unit inside said container, said dental appliance/oral hygiene storage unit being removable through said upper opening.

3. The dental hygiene holding apparatus as recited in claim 1 wherein said container has a supporting ledge below said upper opening, said generally horizontal extension resting on an upper side of said supporting ledge.

4. The dental hygiene holding apparatus as recited in claim 1 wherein said container and said lid are formed from hand blown glass.

5. The dental hygiene holding apparatus as recited in claim 4 wherein said lid has a gripping portion formed therewith and being a part thereof.

6. The dental hygiene holding apparatus as recited in claim 5 wherein said lid has a downward flange therearound to cover the dental appliance, oral hygiene device or dental brush and still allow fresh air thereto.

7. A dental hygiene holding apparatus in which dental appliances, oral hygiene devices or dental brushes may be sterilized in a sterilization bath and stored in said apparatus comprising:
   a container having a flat lower surface, a globular body, and an upper opening large enough to receive dental appliances or oral hygiene devices therethrough;
   a sterilization bath container for holding said sterilization bath therein removably suspended in said upper opening, said sterilization bath container comprising a bowl with an upper rim therearound;
   a generally horizontal extension between said upper opening of said container and said sterilization bath container, said generally horizontal extension having holes therein for suspension of the dental appliances, oral hygiene devices or dental brushes after sterilization in said sterilization bath and wherein said generally horizontal extension extends outwardly from said sterilization bath container over said upper opening when said sterilization bath container is suspended in said upper opening; and
   a lid for simultaneously (a) sealing said sterilization bath in said sterilization bath container, (b) covering the dental appliances, oral hygiene devices or dental brushes as suspended in said holes, and (c) allowing fresh air to the dental appliances, oral hygiene devices or dental brushes, wherein the upper rim of said sterilization bath container holds said lid spaced above said container thereby allowing fresh air to contact the dental appliances, oral hygiene devices or dental brushes.

8. The dental hygiene holding apparatus as recited in claim 7 further including a dental appliance/oral hygiene storage unit inside said container, said dental appliance/oral hygiene storage unit being removable through said upper opening.

9. The dental hygiene holding apparatus as recited in claim 7 wherein said container has a supporting ledge below said upper opening, said generally horizontal extension resting on an upper side of said supporting ledge.

10. The dental hygiene holding apparatus as recited in claim 7 wherein said container and said lid are formed from hand blown glass.

11. The dental hygiene holding apparatus as recited in claim 10 wherein said lid has a gripping portion formed therewith and being a part thereof.

12. The dental hygiene holding apparatus as recited in claim 11 wherein said lid has a downward flange therearound to cover the dental appliance, oral hygiene device or dental brush and still allow fresh air thereto.

* * * * *